US008076389B2

(12) United States Patent
Rao et al.

(10) Patent No.: US 8,076,389 B2
(45) Date of Patent: Dec. 13, 2011

(54) ADHESIVE COMPOSITION FOR HARD TISSUE

(75) Inventors: Prabhakara S. Rao, Maplewood, MN (US); Steven M. Aasen, Woodbury, MN (US); Ahmed S. Abuelyaman, Woodbury, MN (US); Sumita B. Mitra, West St. Paul, MN (US); Bradley D. Craig, Cottage Grove, MN (US); Brian A. Shukla, Woodbury, MN (US); David J. Plaut, Minneapolis, MN (US); Victoria A. Russell, Brooklyn Park, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 32 days.

(21) Appl. No.: 12/520,703

(22) PCT Filed: Dec. 17, 2007

(86) PCT No.: PCT/US2007/087711
§ 371 (c)(1), (2), (4) Date: Jun. 22, 2009

(87) PCT Pub. No.: WO2008/082929
PCT Pub. Date: Jul. 10, 2008

(65) Prior Publication Data

US 2010/0090157 A1 Apr. 15, 2010

Related U.S. Application Data

(60) Provisional application No. 60/877,514, filed on Dec. 28, 2006.

(51) Int. Cl.
*A61C 3/00* (2006.01)

(52) U.S. Cl. ......................... 523/116; 523/118; 523/120

(58) Field of Classification Search .................. 523/118; 428/482, 480; 528/272, 274, 283, 296, 297, 528/302, 306
See application file for complete search history.

(56) References Cited

U.S. PATENT DOCUMENTS

| | | | | |
|---|---|---|---|---|
| 4,259,075 A | | 3/1981 | Yamauchi et al. | |
| 4,298,738 A | | 11/1981 | Lechtken et al. | |
| 4,324,744 A | | 4/1982 | Lechtken et al. | |
| 4,356,296 A | | 10/1982 | Griffith et al. | |
| 4,385,109 A | | 5/1983 | Lechtken et al. | |
| 4,499,251 A | | 2/1985 | Omura et al. | |
| 4,503,169 A | | 3/1985 | Randklev | |
| 4,537,940 A | | 8/1985 | Omura et al. | |
| 4,539,382 A | | 9/1985 | Omura et al. | |
| 4,642,126 A | | 2/1987 | Zador et al. | |
| 4,648,843 A | | 3/1987 | Mitra | |
| 4,652,274 A | | 3/1987 | Boettcher et al. | |
| 4,665,217 A | | 5/1987 | Reiners et al. | |
| 4,695,251 A | | 9/1987 | Randklev | |
| 4,710,523 A | | 12/1987 | Lechtken et al. | |
| 4,719,149 A | | 1/1988 | Aasen et al. | |
| 4,737,593 A | | 4/1988 | Ellrich et al. | |
| 4,752,338 A | | 6/1988 | Reiners et al. | |
| 4,872,936 A | | 10/1989 | Engelbrecht | |
| 5,026,902 A | | 6/1991 | Fock et al. | |
| 5,076,844 A | | 12/1991 | Fock et al. | |
| 5,130,347 A | | 7/1992 | Mitra | |
| 5,154,762 A | | 10/1992 | Mitra et al. | |
| 5,418,301 A | * | 5/1995 | Hult et al. | 525/437 |
| 5,501,727 A | | 3/1996 | Wang et al. | |
| 5,530,038 A | | 6/1996 | Yamamoto et al. | |
| 5,545,676 A | | 8/1996 | Palazzotto et al. | |
| 5,663,247 A | * | 9/1997 | Sorensen et al. | 525/533 |
| 5,760,142 A | * | 6/1998 | Klee | 525/403 |
| 5,834,118 A | * | 11/1998 | R.ang.nby et al. | 428/482 |
| 6,030,606 A | | 2/2000 | Holmes | |
| 6,251,963 B1 | | 6/2001 | Kohler et al. | |
| 6,331,080 B1 | | 12/2001 | Cole et al. | |
| 6,387,981 B1 | | 5/2002 | Zhang et al. | |
| 6,444,725 B1 | | 9/2002 | Trom et al. | |
| 6,458,868 B1 | | 10/2002 | Okada et al. | |
| 6,528,555 B1 | | 3/2003 | Nikutowski et al. | |
| 6,572,693 B1 | | 6/2003 | Wu et al. | |
| 6,624,236 B1 | | 9/2003 | Bissinger et al. | |
| 6,852,795 B2 | | 2/2005 | Bissinger et al. | |
| 6,852,822 B1 | | 2/2005 | Bissigner et al. | |
| 6,953,832 B2 | | 10/2005 | Moszner et al. | |
| 7,090,721 B2 | | 8/2006 | Craig et al. | |
| 7,090,722 B2 | | 8/2006 | Budd et al. | |
| 7,156,911 B2 | | 1/2007 | Kangas et al. | |
| 7,365,105 B2 | * | 4/2008 | Kiefer-Liptak | 522/121 |
| 7,649,029 B2 | | 1/2010 | Kolb et al. | |
| 2003/0166737 A1 | | 9/2003 | Dede et al. | |
| 2003/0166740 A1 | | 9/2003 | Mitra et al. | |
| 2003/0195273 A1 | | 10/2003 | Mitra et al. | |
| 2004/0206932 A1 | | 10/2004 | Abuelyaman | |
| 2005/0070627 A1 | | 3/2005 | Falsafi et al. | |
| 2005/0175965 A1 | * | 8/2005 | Craig et al. | 433/215 |
| 2005/0175966 A1 | * | 8/2005 | Falsafi et al. | 433/215 |
| 2005/0176844 A1 | * | 8/2005 | Aasen et al. | 523/118 |

(Continued)

FOREIGN PATENT DOCUMENTS

| | | |
|---|---|---|
| EP | 0201031 | 5/1985 |

(Continued)

*Primary Examiner* — Robert J Hill, Jr.
*Assistant Examiner* — Peter A Salamon
(74) *Attorney, Agent, or Firm* — Pamela L. Stewart

(57) ABSTRACT

An adhesive composition including an etchant for a hard tissue surface, at least one multifunctional crosslinkable (meth)acrylate monomer with a functionality greater than 4, and water. The adhesive composition is a water-in-oil emulsion.

10 Claims, No Drawings

U.S. PATENT DOCUMENTS

2006/0204676 A1 9/2006 Jones et al.
2007/0066748 A1 3/2007 Lewandowski et al.
2007/0141524 A1 6/2007 Brennan et al.
2007/0142494 A1 6/2007 Kalgutkar et al.
2007/0142497 A1 6/2007 Kalgutkar et al.
2007/0142498 A1 6/2007 Brennan et al.
2007/0248927 A1* 10/2007 Luchterhandt et al. ........... 433/9
2008/0299519 A1 12/2008 Craig et al.
2009/0075239 A1 3/2009 Abuelyaman
2010/0069527 A1* 3/2010 Arata et al. ................... 523/118

FOREIGN PATENT DOCUMENTS

EP 0173567 3/1986
EP 0201778 11/1986
EP 0373384 6/1991
EP 712622 5/1996
EP 1051961 11/2000
EP 1498098 1/2005
EP 1849449 10/2007
WO WO 00/38619 7/2000
WO WO 00/42092 7/2000
WO WO 01/07444 2/2001
WO WO 01/30305 5/2001
WO WO 01/30306 5/2001
WO WO 01/30307 5/2001
WO WO 01/92271 12/2001
WO WO 03/013379 2/2003
WO WO 03/063804 8/2003
WO WO 2006/014597 2/2006

* cited by examiner

ADHESIVE COMPOSITION FOR HARD TISSUE

CROSS REFERENCE TO RELATED APPLICATIONS

This application is a national stage filing under 35 U.S.C. 371 of PCT/US2007/087711, filed Dec. 17, 2007, which claims priority to U.S. Application No. 60/877,514, filed Dec. 28, 2006, the disclosure of which is incorporated by reference in its/their entirety herein.

TECHNICAL FIELD

The present disclosure relates to adhesive compositions for bonding to and/or repairing hard tissue, as well as to methods for making and using them.

BACKGROUND

To repair hard tissue, particularly human and animal dental structures, such as tooth structures (e.g., dentin or enamel), first an adhesive is applied on the surface of the dental structure. Next, a restorative dental material may be applied on the adhesive, or the adhesive may be used alone without the restorative dental material, to repair or reconstruct the dental structure. Similarly, adhesives may also be used to bond dental materials (e.g., orthodontic appliances, generally utilizing an orthodontic adhesive) to a surface of a dental structure.

Various pretreatment processes can be used to promote the bonding of adhesives to dental structures such as dentin or enamel. Such pretreatment steps include etching, for example, using inorganic or organic acids, followed by priming to improve the bonding between the surface of the dental structure and the overlying adhesive. Following the etching and priming steps, an adhesive is applied and hardened to attach the dental restorative or orthodontic appliance. As a result, dental restoration procedures and the application of orthodontic appliances are typically multi-step processes.

Some "one-step" adhesives purport to provide etching, priming and adhering in a single step. However, a two step process is often carried out, including an initial application of water on the surface of the dental structure, followed by application of the adhesive and subsequent curing. Other "one step" primers are formed by mixing compartmentalized precursor ingredients such as, for example, water, adhesion monomers and an etchant, before they are applied on the dental structure surface.

SUMMARY

If water, adhesion monomers and etchant are provided to the dental practitioner in separate containers, a separate mixing step is required prior to application of the dental adhesive composition to the dental structure surface. In addition to being rather complex and messy, inaccuracies inherent in the mixing process can result in levels of adhesion that vary from patient to patient. Further, even if the dental structure surface is treated with water or other liquids prior to application of the dental adhesive composition, variations in the amount of wetting may occur, which again result in variations in adhesion from patient to patient. Wetting requirements also require the dental adhesive composition to be applied in a relatively narrow time frame, or conditions on the dental structure surface may change, resulting in unpredictable levels of adhesion.

The present disclosure is directed to adhesive compositions for hard tissues that provide water, an etchant, and crosslinkable adhesive-forming monomers in a single container. Using this adhesive composition, it is not necessary for the practitioner to apply water to a surface of a hard tissue structure such as, for example, a dental structure, prior to repair or application of a restorative material. A single-step adhesion process made possible by these adhesive compositions combines etching, priming and adhering into a single step without requiring the practitioner to premix adhesive components or to wet the surface of the hard tissue structure. The components of the compositions are provided in a single container, and they have an extended shelf life, which means that this predictable etching, priming and adhering performance is maintained, compared to conventional compositions, over an extended period of time.

In one aspect, the present disclosure is directed to an adhesive composition including an etchant for a hard tissue surface, at least one multifunctional (meth)acrylate monomer with a functionality greater than 4, and water, wherein the adhesive composition is a water-in-oil emulsion.

In another aspect this disclosure is directed to a dental adhesive composition, including: (a) 5-25 wt % of a multifunctional (meth)acrylate monomer with a functionality greater than 4, wherein the monomer is derived from a hyperbranched dendritic polyester polyol; (b) 10-25 wt % water; (c) 0-25 wt % of a co-solvent selected from the group consisting of ethyl alcohol, ethyl acetate, and isopropanol; and (d) 5-11 wt % of an etchant for at least one of dentin and enamel, wherein the dental adhesive composition is a microemulsion.

In another aspect, this disclosure is directed to a method including applying to a dental structure surface an adhesive composition including (i) 8-25 wt % of a multifunctional (meth)acrylate monomer with a functionality greater than 4, wherein the monomer is derived from a hyperbranched dendritic polyester polyol, (ii) 10-25 wt % water, (iii) 0-25 wt % of a co-solvent selected from the group consisting of ethyl alcohol, ethyl acetate, and isopropanol, and (iv) 5-11 wt % of an etchant for at least one of dentin and enamel, wherein the adhesive composition is a microemulsion.

Other features, objects, and advantages of the invention will be apparent from the following detailed description thereof, and from the claims.

DETAILED DESCRIPTION

In one aspect, this disclosure is directed to an adhesive composition for bonding to and repairing hard tissues such as, for example, bones, nails, and teeth of humans and animals. The adhesive composition is particularly well suited for bonding to and repair of dental structures such as dentin or enamel. The adhesive composition includes water, an etchant suitable for a hard tissue structures, and an adhesive including at least one multifunctional dendritic or hyperbranched (meth)acrylate monomer with a functionality greater than 4. The composition is typically a water-in-oil emulsion, preferably a microemulsion with a water droplet size of less than about 100 nm.

The adhesive composition is self-adhesive, which refers to a composition capable of bonding to a hard tissue structure surface without pretreating the surface with a separate primer, bonding agent, or wetting agent such as water. The adhesive composition is also self-etching, and requires no separate etchant.

As used herein, adhesive refers to a component of the adhesive composition that may be used as a pre-treatment on a surface of a hard tissue structure, particularly a dental structure surface (e.g., a tooth). The adhesive may be used alone to repair a dental structure, or may be used to adhere a dental material such as, for example, a restorative, an orthodontic appliance (such as a bracket), or an orthodontic adhesive to the dental structure.

The adhesive composition includes at least one multifunctional dendritic or hyperbranched (meth)acrylate monomer. When cured or hardened, the multifunctional groups in these compounds form a crosslinked structure which adheres to a hard tissue structure surface, particularly a dental structure surface. Following at least a partial curing or hardening step, multiple functional groups remain that are capable of forming additional crosslinks in subsequent curing or hardening steps to adhere to a dental material such as, for example, a restorative.

The multifunctional monomers used in the adhesive are crosslinkable (meth)acrylate monomers with functionality greater than 4. These compounds may be dendritic or hyperbranched, which means that they have multiple functional groups available for curing and for the formation of crosslinks. As used herein, "(meth)acryl" is a shorthand term referring to "acryl" and/or "methacryl." The (meth)acrylate monomers preferably have an a functionality of about 4 to about 32, more preferably about 6 to about 16, and most preferably about 8 to about 16.

A first group of crosslinkable (meth)acrylate monomers suitable for use as the adhesive include multifunctional acrylates derived from hyperbranched (dendritic) polyester polyols. Examples include the compounds available from Sartomer Corp., Exton Pa., under the trade designation CN2300 (8 alcohol groups), CN 2301 (9 alcohol groups) and CN 2302 (16 alcohol groups). Preferred multifunctional acrylates have about 8 to about 16 functional acrylate groups, most preferably about 8 to about 12 functional acrylate groups.

A second class of materials suitable for use as the adhesive include multifunctional methacrylates derived from hyperbranched (dendritic) polyester polyols available under the trade designations BOLTORN H2004 (6 alcohol groups), H2003 (12 alcohol groups), U3000 (14 alcohol groups), H311 (23 alcohol groups), and H30 (32 alcohol groups) from Perstorp Polyols, Inc., Toledo Ohio. Preferred multifunctional methacrylates have about 8 to about 16 functional methacrylate groups, most preferably about 9 to about 12 functional methacrylate groups.

These multifunctional acrylate and methacrylate compounds are typically made by, for example, reacting the terminal hydroxyl groups in the dendritic or hyperbranched polyester polyols with, for example, isocyanatoethyl methacrylate (IEM), in the presence of a catalyst such as dibutyl tin dilaurate.

The multifunctional dendritic or hyperbranched (meth) acrylate compound is typically present in the adhesive composition at a concentration of about 8 wt % to about 25 wt %, more preferably about 10 wt % to about 25 wt %, based on the total weight of the composition.

As used herein, the term "etchant" refers to an acidic composition that is capable of fully or partially solubilizing (i.e., etching) a hard tissue structure surface, particularly a dental structure surface. The etching effect can be visible to the naked human eye and/or instrumentally detectable (e.g., by light microscopy). Suitable etchants may be selected from a wide variety of polymerizable or non-polymerizable compounds with acid functionality, which includes monomers, such as ethylenically unsaturated monomers, oligomers, and polymers having acid and/or acid-precursor functionality, including such polymers also having ethylenic unsaturation. Acid-precursor functionalities include, for example, anhydrides, acid halides, and pyrophosphates.

Ethylenically unsaturated compounds with acid functionality suitable for use as the etchant include, for example, .alpha., .beta.-unsaturated acidic compounds such as acrylic acid, methacrylic acid, 4-(methacryloyloxyethyl)trimellitic acid ("4-MET"), 4-(methacryloyloxyethyl)trimellitic anhydride ("4-META"), glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis ((meth)acryloxypropyl) phosphate, bis((meth)acryloxy)propyloxy phosphate, (meth)acryloxyhexyl phosphate, bis ((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or trimethacrylates, poly(meth)acrylated oligomaleic acid, poly (meth)acrylated polymaleic acid, poly(meth)acrylated poly (meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable resin system. Also monomers, oligomers, and polymers of unsaturated carboxylic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one —P(OH) moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Published Patent Application Nos. 2007/0142494, 2007/0142497, 2007/0142498, 2007/0141524, and 2007/0066748.

Compositions of the present invention can include non-polymerizable compounds with acid functionality. Examples of such compounds include formic acid, trifluoroacetic acid, acetic acid, toluenesulfonic acid, and benzoic acid. Exemplary non-polymerizable compounds with acid functionality are described in U.S. Pat. No. 4,719,149 (Aasen, et al.).

Preferably, the compositions of the present invention include about 5 wt % to about 11 wt % of the etchant, more preferably about 6 wt % to about 11 wt %. Preferred etchants include 6-methacryloxyhexyl phosphate (MHP), 10-methacryloxydecyl phosphate (MDP), and the like.

The adhesive composition also includes sufficient water and an optional co-solvent such that the adhesive composition exists as a water-in-oil emulsion. As used herein, a "water-in-oil" emulsion refers to a water-in-oil mixture in which the oil forms a continuous phase and the water is in discontinuous droplets. A water-in-oil emulsion can be distinguished from an oil-in-water emulsion by using an electrical emulsion tester. An oil-in-water emulsion will conduct electricity with relatively low resistance since water forms its external or continuous phase, whereas a water-in-oil emulsion will not conduct, or very poorly conduct, electricity.

The oil phase in a water-in-oil emulsion refers to all components in the formulation that individually exceed their solubility limit in the water phase; these are materials that generally have solubilities of less than about 5%, preferably less than about 2%, and more preferably less than about 1% in distilled water. However, water phase components such as salts may decrease the solubility of certain oils resulting in their partitioning into the oil phase. The water phase in a water-in-oil emulsion refers to the water present and any components that are water soluble, i.e., have not exceeded their solubility limit in water.

The adhesive composition is preferably a microemulsion, which refers to emulsions that are thermodynamically favored and form spontaneously without energy required from mechanical force such as high speed agitation. The theory of microemulsions is available in the scientific literature including, for example, Leung et al, Chapter 9 in "Surfactants in Chemical Process Engineering," Marcel Dekker (1988); Overbeek et al., "Surfactants" in Microemulsions, Academic Press (1984); Safran et al., Phys. Rev. Lett., 50:1930 (1983); Ruckenstein et al., J. Chem. Soc. Faraday Trans, 2, 71:1690 (1975); and Ostrovsky et al., J. Colloid. Interface Sci., 102:206 (1984); and Chapter 6 of "Microemulsions", pp. 138-155 (Holmberg et al.) in Surfactants and Polymers in Aqueous Solution; Second Edition, John Wiley & Sons, (2003; Reprinted with corrections in 2004).

The water and oil phases of the microemulsion do not separate upon extended storage, and the microemulsion remains chemically and physically stable without dispersing aids and periodic high speed agitation. Preferred microemulsions are storage stable without phase separation for at least 4-5 months at 45° C., and at least 2 years, and preferably at least 3 years, at room temperature. The shelf-life of an adhesive composition is typically measured by determining if the aged composition provides acceptable bond strengths when the aged composition is bonded to a hard tissue structure surface.

The adhesive composition microemulsions are typically substantially clear, which means that they preferably include no water droplets sufficiently large to scatter visible light. Typically, the water-in-oil microemulsions herein have a water droplet size of less than about 100 nm, preferably less than about 50 nm, and more preferably less than about 30 nm. The water droplet size may be evaluated by, for example, X-ray scattering. The microemulsions also have a low viscosity, which makes it relatively simple to apply them on dental material.

To provide a physically and chemically stable microemulsion, the adhesive composition preferably includes about 10 wt % to about 25 wt % water, preferably about 13 wt % to about 22 wt %, and more preferably about 14 wt % to about 18 wt %. The dental adhesive composition may further optionally include up to about 25 wt %, preferably about 15 wt % to about 22 wt %, of a co-solvent. Suitable co-solvents include, for example, organic compounds that are at least partially miscible with water. Suitable co-solvents may contain, for example, alcohol, ketone, ester, ether, or amide groups, or they may contain more than one of these groups in the same co-solvent compound. Examples of suitable co-solvents include ethyl alcohol, ethyl acetate, acetone, methyl ethyl ketone, and isopropanol. Ethyl alcohol is particularly preferred to provide microemulsions with enhanced physical stability.

In a typical procedure for making a water-in-oil microemulsion, the water is added slowly with mixing as a final step to the remaining components of the adhesive composition. The water can be "titrated" such that the mixture remains clear (i.e., not turbid). Often during this "titration" procedure the microemulsion forms spontaneously prior to the point of initial turbidity. If, during the "titration" procedure, the mixture becomes turbid, it can often be made clear again by the addition of small amounts of the optional co-solvent. Typically, the microemulsion is formed by simple mixing and the oil and water-components of the composition do not need to be pre-mixed separately or heated prior to the addition of the water and/or co-solvent.

The adhesive composition preferably includes one or more second polymerizable components that, when polymerized, harden and enhance the adhesive strength of the composition. The second polymerizable components may be monomers, oligomers, or polymers that may be monofunctional or multifunctional.

In certain embodiments, the second polymerizable components are photopolymerizable, i.e., contain a photopolymerizable component and a photoinitiator (i.e., a photoinitiator system) that upon irradiation with actinic radiation initiates the polymerization (or hardening) of the composition. Such photopolymerizable components can be free radically polymerizable.

In other embodiments, the second polymerizable components are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable components are sometimes referred to as "self-cure" compositions and may include glass ionomer cements, resin-modified glass ionomer cements, redox cure systems, and combinations thereof.

Preferably, the adhesive compositions include at least about 5% by weight, more preferably at least about 10% by weight, and most preferably at least about 15% by weight, of the second polymerizable component, based on the total weight of the unfilled composition. Preferably, the dental adhesive compositions include at most 95% by weight, more preferably at most 90% by weight, and most preferably at most 80% by weight of the second polymerizable component.

Suitable photopolymerizable components may include photopolymerizable components (e.g., compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable components may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. Mixtures of ethylenically unsaturated compounds can be used if desired.

Preferred photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 350 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. pat. Publication No. 2003/0166737 (Dede et al.).

Other suitable photoinitiators for polymerizing free radically photopolymerizable compositions include the class of acylphosphine oxides that typically have a functional wavelength range of 380 nm to 1200 nm. Preferred acylphosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available acylphosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)pheny-1 phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the acylphosphine oxide initiator is present in the photopolymerizable composition in catalytically effective amounts, such as from 0.1 wt % to 5.0 wt %, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

The chemically polymerizable components may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic acid salts, such as p-toluenesulfinic acid salts and benzenesulfinic acid salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. pat. Publication No. 2003/0195273 (Mitra et al.).

The reducing and oxidizing agents are present in amounts sufficient to permit an adequate free-radical generation rate. This can be evaluated by combining all of the ingredients of the polymerizable composition except for the optional filler, and observing whether or not a hardened mass is obtained.

Preferably, the reducing agent is present in an amount of at least 0.01% by weight, and more preferably at least 0.1% by weight, based on the total weight (including water) of the components of the polymerizable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

The adhesive composition may optionally include additional components to improve and/or modify its properties.

For example, the adhesive composition may optionally include about 8 wt % to about 10 wt % of a polymerizable monomer such as, for example, bis-GMA (bisphenol A diglycidyl methacrylate), UDMA [(2,2,4-trimethylhexamethylenebis(2-carbamoyloxyethyl) dimethacrylate), 9G (poly[ethylene glycol (400)] dimethacrylate and the like to enhance adhesion to dental structures and dental surfaces.

In addition, the dental adhesive composition may further optionally include about 6 wt % to about 15 wt % of a hydrophilic polymerizable monomer such as, for example, HEMA (2-hydroxyethyl methacrylate), to enhance penetration into hard tissue structures and surfaces, and to enhance overall bond strength.

Further, the adhesive composition may optionally include an additional supplemental acidic monomer such as methacrylic acid, 1,3 butanediol dimethacrylate, 2-hydroxyethyl methacrylate and the like to enhance bond strength.

The adhesive composition may further optionally include a polymerizable monomer to provide resistance to hydrolysis. Suitable compounds for hydrolysis resistance include, for example, monofunctional or multifunctional polymerizable amide monomers. Examples of polymerizable amide monomers include monofunctional or multifunctional (meth)acrylamides. Examples of monofunctional polymerizable (meth) acrylamide monomers include N-ethyl methacrylamide, N-butyl methacrylamide, N-decyl methacrylamide, N-ethyl acrylamide, N-butyl acrylamide, N-decyl acrylamide, and N-hydroxyalkyl (meth)acrylamides such as, for example, such as N-(2-hydroxylpropyl) methacrylamide. Examples of multifunctional polymerizable amide monomers include multifunctional (meth)acrylamide monomers such as those disclosed in U.S. Pat. No. 6,953,832 (Moszner et al.).

The adhesive compositions can also optionally contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodal or polymodal (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 0.1 micrometers, and more preferably less than 0.075 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; Mania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially preferred in certain embodiments.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Other suitable fillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. Nos. 7,090,721; 7,090,722; and 7,156,911.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., wherein the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition.

In some embodiments, the adhesive compositions have an initial color remarkably different than dental structures. Color is preferably imparted to the composition through the use of a photobleachable dye. The composition preferably includes at least 0.001% by weight photobleachable dye, and more preferably at least 0.002% by weight photobleachable dye, based on the total weight of the composition. The composition preferably includes at most 1% by weight photobleachable dye, and more preferably at most 0.1% by weight photobleachable dye, based on the total weight of the composition. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of AE* is determined, which indicates the total color change in a 3-dimensional color space. The human eye can detect a color change of approximately 3.DELTA.E* units in normal lighting conditions. The dental compositions of the present invention are preferably capable of having a color change, .DELTA.E*, of at least 10; more preferably, .DELTA.E* is at least 20; most preferably .DELTA.E* is at least 40.

If desired, the adhesive compositions can contain additives such as indicators, dyes, pigments, inhibitors, accelerators, viscosity modifiers, wetting agents, tartaric acid, chelating agents, buffering agents, stabilizers, and other similar ingredients that will be apparent to those skilled in the art. Additionally, medicaments or other therapeutic substances can be optionally added to the dental adhesive compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result.

Methods of Use

Exemplary methods of using the adhesive compositions are described in the Examples below, particularly in repairing and/or restoring dental structures. Generally, in dental applications the adhesive composition may be applied to an untreated surface of any dental structure, which may be dry or not dry, using conventional techniques. Dental structures include tooth structures (e.g., enamel, dentin, and cementum) and bone. The untreated dental surface preferably has not been pre-treated with an etchant, primer, bonding agent or water prior to application of the adhesive composition.

Prior to application of the adhesive composition, the surface of the dental structure may be cut or uncut. As used herein, an uncut dental structure surface refers to a dental structure surface that has not been prepared by cutting, grinding, drilling, etc.

The dental structure surface is preferably dry, which refers to a surface of a dental structure that has been dried (e.g., air dried) and does not have present visible water.

The method of application may vary widely, but typically the dental adhesive composition may be applied directly on the dental structure surface with a delivery system, for example, including an applicator such as a brush. Following a sufficient treatment time, typically about 5 seconds to about 30 seconds, the composition may optionally be air-dried under a gentle air flow. Typical air drying requires about 5 seconds to about 30 seconds.

Following application, the adhesive composition is at least partially hardened or cured for a time sufficient to form a film-like layer on the dental structure surface. As used herein, hardening or curing are used interchangeably to refer to polymerization and/or crosslinking reactions including, for example, photopolymerization reactions and chemical polymerization techniques (e.g., ionic reactions reactions or chemical reactions forming radicals effective to polymerize ethylenically unsaturated compounds) involving one or more materials included in the composition. In one embodiment, if the adhesive composition includes a photopolymerizable compound, the curing step requires exposing the adhesive composition to light of a suitable wavelength, typically about 380-450 nm, depending on the photoinitiator system used in the composition. Suitable lamps include, for example, those available from 3M ESPE Dental Products, St. Paul, Minn., under the trade designations ELIPAR.

The partially cured composition forms a layer of a film-like reaction product of the dental adhesive composition and the material making up the dental structure surface (e.g. dentin/enamel). While not wishing to be bound by any theory, presently available evidence indicates that the dendritic, hyperbranched structure of the multifunctional (meth)acrylate adhesive microemulsions penetrate the dental structure surface and form a bond at an intercellular level. This bond has highly dense crosslinked domains, but following the partial cure the multifunctional (meth)acrylates retain sufficient residual functionality for additional crosslinking. Typically, the bond between the film-like layer and the dental structure surface (when measured by pulling a loop of, for example, orthodontic wire that is placed around a pad of cured composite dental restorative composition that is adhered to the surface of a dental structure such as enamel) is about 5 to about 30 MPa, more preferably about 7 to about 30 MPa, and most preferably about 10 to about 30 MPa.

Finally, the partially cured adhesive composition is fully cured. At any time prior to the full curing step, a dental material (e.g., a dental restorative such as, for example, those available from 3M ESPE Dental Products, St. Paul, Minn. under the trade designation FILTEK Z250 UNIVERSAL RESTORATIVE) may optionally be applied to the layer of the uncured or partially cured adhesive composition. In one embodiment, the uncured or partially cured adhesive composition underlying the restorative is fully cured by applying 380-450 nm light for about 20 seconds.

Methods of bonding a dental material to a dental structure surface preferably result in a bond to enamel or dentin (or preferably both), of at least 7 MPa, more preferably at least 15, MPa, and most preferably at least 20 MPa.

For dental applications, the adhesive composition described herein may be provided pre-packaged in bulk form, or may be provided in kit form coupled with ancillary equipment useful to dental professionals including, for example, delivery systems including brushes or other applicators, and restoratives.

Some embodiments of the present invention are illustrated by the following examples. It is to be understood that the particular examples, materials, amounts, and procedures are to be interpreted broadly in accordance with the scope and spirit of the invention as set forth herein. Unless otherwise indicated, all parts and percentages are on a weight basis, all water is deionized water, and all molecular weights are weight average molecular weight.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

Unless otherwise noted, all solvents and reagents were or can be obtained from Sigma-Aldrich Corp., St. Louis, Mo.

As used herein,

"IEM" refers to 2-isocyanatoethyl methacrylate;

"BisGMA" refers to 2,2-bis[4-(2-hydroxy-3-methacryloyloxypropoxy)phenyl]propane;

"CPQ" refers to camphorquinone;

"EDMAB" refers to ethyl 4-(N,N-dimethylamino)benzoate;

"DPIHFP" refers to diphenyl iodonium hexafluorophosphate;

"BH2003" refers to a dendritic polyol calculated as having hydroxyl functionality of approximately 12, available under the trade designation "BOLTORN H2003" from Perstorp Polyols, Inc., Toledo, Ohio;

"BH2004" refers to a dendritic polyol calculated as having hydroxyl functionality of approximately 6, available under the trade designation "BOLTORN H2004" from Perstorp Polyols, Inc., Toledo, Ohio;

"BU3000" refers to a dendritic polyol calculated as having hydroxyl functionality of approximately 14, available under the trade designation "BOLTORN U3000" from Perstorp Polyols, Inc., Toledo, Ohio;

"BW3000" refers to a dendritic polyol available under the trade designation "BOLTORN W3000" from Perstorp Polyols, Inc., Toledo, Ohio;

"TMPTMA" refers to trimethylolpropane trimethacrylate;

"MHP" refers to 6-methacryloxyhexyl phosphate, prepared as described in U.S. Patent Publication No. 2005/0175966;

"MDP" refers to 10-methacryloxydecyl phosphate, prepared as described in U.S. Patent Publication No. 20050175966;

"MOP" refers to 8-methacryloxyoctyl phosphate, prepared from 1,8-octanediol using the method essentially as described for the preparation of MHP and MDP in U.S. Patent Publication No. 20050175966;

"HEMA" refers to 2-hydroxyethyl methacrylate;

"1,3-BDDM" refers to 1,3-butanediol dimethacrylate;

"MA" refers to methacrylic acid;

"TEGDMA" refers to triethyleneglycol dimethacrylate;

"2-TMSEM" refers to 2-(trimethoxysiloxy)ethyl methacrylate (obtained from Polysciences Inc., Warrington, Pa.;

"CN2300" refers to a polyester acrylate oligomer available under the trade designation "CN2300" from Sartomer Co., Inc., Exton, Pa.;

"CN2301" refers to a polyester acrylate oligomer available under the trade designation "CN2301" from Sartomer Co., Inc., Exton, Pa.;

"CN2302" refers to a polyester acrylate oligomer available under the trade designation "CN2302" from Sartomer Co., Inc., Exton, Pa.;

"2HPM" refers to N-2-hydroxypropyl methacrylamide;

"3KMPS" refers to potassium 3-(methacryloyloxy)propanesulfonate;

"Zirconia sol" refers to an aqueous zirconia sol prepared, for example, as described in Preparative Example 1.

"SR534" refers to a multifunctional acrylic ester obtained under the trade designation SR534 from Sartomer Co., Inc., Exton, Pa.;

"DMAPM" refers to N,N-dimethylaminopropyl methacrylamide;

"EDMA" refers to 2-ethyl-9,10-dimethoxyanthracene;

"AA/ITA/IEM" refers to the polymer made as described in Example 11 of U.S. Pat. No. 5,130,347 (Mitra).

Adhesion Test

Adhesive shear bond strength to enamel or dentin for a given test sample was evaluated by the following procedure.

Bovine incisal teeth, free of soft tissue, were embedded in circular acrylic disks. The embedded teeth were stored in water in a refrigerator prior to use. In preparation for adhesive testing, the embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process. The polished teeth were stored in deionized water and used for testing within 2 hours after polishing. The teeth were allowed to warm in a 36° C. oven to between room temperature (about 23° C.) and 36° C. before use.

An adhesive emulsion test sample was applied with a dental applicator brush over the entire surface of the prepared enamel or dentin surface for approximately 20 seconds. After an additional approximately 10 seconds, the coated enamel or dentin, the coating was exposed to a stream of air for approximately 10 seconds. Then the adhesive coating was light cured for 10 seconds with an XL 3000 dental curing light (3M ESPE Dental Products, St. Paul, Minn.). A 2.5-mm thick cylindrical poly(tetrafluoroethylene) mold having an inside diameter of approximately 4.7 millimeters was placed over the coating on the tooth such that the opening in the mold exposed part of the adhesively prepared tooth surface. A composite restorative, A2 shade of FILTEK Z250 Universal Restorative (3M ESPE Dental Products, St. Paul, Minn.), was placed in the opening such that the opening was completely filled. The restorative was then light cured for 20 seconds to form a "pad" that was adhesively attached to the tooth.

The adhesive strength of a cured test example was evaluated by mounting the assembly (described above) in a holder clamped in the jaws of a Model 4505 testing instrument (available from Instron Corp. Canton, Mass.) with the polished tooth surface oriented parallel to the direction of pull. A loop of orthodontic wire (0.44-mm diameter) was placed around the cured pad of composite restorative adjacent. The ends of the orthodontic wire were clamped in the jaw of the INSTRON instrument and the wire was pulled at a crosshead speed of 2 millimeters per minute. The force at which the bond failed was recorded, and this value was converted to a force per unit area (units of MPa) using the surface area of the pad. In the Examples, each value of adhesion to enamel and to dentin represents the average value of 4 or 5 replicates.

Preparative Example 1

Preparation of Zirconia Sol

An approximately 12-inch section of dialysis tubing having a nominal flat width of 32 mm, a nominal diameter of 20.4 mm, and a molecular weight cutoff of 12,000 to 14,000 (obtained under the trade designation SPECTRA/POR from VWR International, Inc., West Chester, Pa.) was immersed in distilled water for 48 hours. The dialysis tubing was then charged with approximately 50 mL of a zirconia sol (prepared as described in U.S. Patent Application Publication No. 20060204676). Both ends of the dialysis tubing were sealed and then the tubing was suspended in distilled water (approximately 4 liters) in a beaker for approximately 24 hours. During this time, the water in the beaker was removed and replaced with distilled water six times. The concentration of this dialyzed zirconia sol was determined by drying a small weighed portion of the sol in a dish in a forced air oven. Sufficient distilled water was then added to the remaining dialyzed zirconia sol to provide a diluted sol having a concentration of 25 weight percent. A portion of this diluted sol (50 g) was transferred to a glass jar. As the diluted sol was magnetically stirred, methacrylic acid (1.17 g) was slowly added (over approximately five minutes) to the sol. The mixture was then sonicated for ten minutes using a Model 350 SONIFIER sonicator (obtained from Branson Ultrasonics Corp., Danbury, Conn.), with the jar cooled in the circulating cooling water bath of the sonicator. The sol was stored in a refrigerator and was sonicated as described for approximately five minutes before each use.

Examples 1-6

Preparation of Dendritic Methacrylates

For each of Examples 1-5, a mixture of a dendritic polyol and IEM, in the amounts given in Table 1 (the amounts calculated for the desired stoichiometry), and one drop of dibutyltin dilaurate, was stirred in a reaction flask that was partially immersed in a water bath at room temperature. Evolution of bubbles from the mixture began after approximately 10-15 minutes of stirring. After the evolution of bubbles ceased, each mixture was stirred for approximately 15 minutes longer to afford the product. The product of each of Examples 1-3, 5, and 6 was analyzed by $^{1}H$ NMR to determine the number of methacrylate groups per molecule. The components and results of each reaction of Examples 1-5 is given in Table 1. In Table 1, "Methacrylate groups" refers to the number of methacrylate groups per molecule.

TABLE 1

Data for Examples 1-5

| Example | Dendritic polyol (Weight) | Weight IEM | Methacrylate groups |
|---|---|---|---|
| 1 | BH2003 (20 g) | 5 g | 4 |
| 2 | BH2003 (20 g) | 10 g | 8 |
| 3 | BH2003 (20 g) | 15 g | 12 |
| 4 | BU3000 (20 g) | 1.2 g | 2.5 |
| 5 | BW3000 (10 g) | 0.7 g | 4 |
| 6 | BW3000 (10 g) | 1.4 g | 8 |

Examples 7-16

Preparation of Dental Adhesive Microemulsions

Components of the dental adhesive microemulsions of Examples 7-16 include those given in Table 2. The dental adhesive microemulsions of Examples 7-16 were prepared by combining the components, except water, in the amounts given in Table 2, in a vial and using a vortex mixer to prepare a homogeneous mixture. Then CPQ (0.2 g), EDMAB (0.16 g), and DPIHFP (0.13 g) were each added to the mixture and the vortex mixer was again used to prepare a homogeneous mixture. Water was then added dropwise with gentle mixing to afford the dental adhesive microemulsions. In Table 2, "n/a" means that the component was not combined in the dental adhesive microemulsion.

TABLE 2

Compostions of Examples 7-16

| Component | Example 7 | 8 | 9 | 10 | 11 | 12 | 13 | 14 | 15 | 16 |
|---|---|---|---|---|---|---|---|---|---|---|
| TMPTMA | 1.4 g | 0.7 g | 0.7 g | 0.7 g | 1.0 g | 1.0 g | 1.0 g | 1.0 g | 1.4 g | 1.4 g |
| MHP | 0.9 g | 0.7 g | 0.7 g | 0.7 g | 1.2 g | 1.2 g | 1.2 g | 1.5 g | 1.5 g | 1.5 g |
| TEGDMA | 1.2 g | 1.4 g | 1.4 g | 1.4 g | 1.4 g | 1.4 g | 1.4 g | 1.0 g | 1.0 g | 1.0 g |
| BisGMA | 1.2 g | 1.4 g | 1.4 g | 1.4 g | 1.4 g | 1.4 g | 1.4 g | 1.5 g | 2.0 g | 2.0 g |
| Ethanol | 3.0 g | 2.4 g | 2.4 g | 2.4 g | 2.4 g | 2.4 g | 2.4 g | 2.5 g | 2.5 g | 2.5 g |
| HEMA | 0.7 g | 1.0 g | 1.0 g | 1.0 g | 1.0 g | 1.0 g | 1.0 g | 1.5 g | 1.5 g | 1.5 g |
| Water | 3.0 g | 2.7 g | 2.2 g | 3.0 g | 2.7 g | 2.2 g | 3.0 g | 2.5 g | 3.0 g | 3.0 g |
| 1,3-BDDM | 0.8 g | 0.7 g | 0.7 g | 0.7 g | 0.5 g | 0.5 g | 0.5 g | n/a | n/a | n/a |
| MA | 0.5 g | 0.5 g | 0.5 g | 0.5 g | 0.5 g | 0.5 g | 0.5 g | 0.5 g | 0.5 g | 0.5 g |
| 2-TMSEM | n/a | n/a | n/a | n/a | n/a | n/a | n/a | 0.2 g | n/a | n/a |
| Example 1 | 1.0 g | 1.5 g | n/a | n/a | n/a | n/a | n/a | 1.0 g | n/a | n/a |
| Example 2 | n/a | n/a | 1.5 g | 1.5 g | n/a | n/a | 1.0 g | 1.5 g | 1.5 g | n/a |
| BH2003 | n/a | n/a | n/a | 1.0 g | n/a | n/a | n/a | n/a | n/a | n/a |
| Example 3 | n/a | n/a | n/a | n/a | n/a | n/a | n/a | n/a | 1.0 g | 2.5 |
| Example 4 | n/a | n/a | n/a | n/a | 2.0 g | n/a | n/a | n/a | n/a | n/a |
| Example 5 | n/a | n/a | n/a | n/a | n/a | 2.0 g | 1.0 g | n/a | n/a | n/a |

The dental adhesive microemulsions of Examples 7-16 were evaluated using the Adhesion Test described above. The Adhesion Test was conducted using microemulsions stored for a time and at a temperature as indicated in Table 3. The data are given in Table 3. In Table 3, "RT" means room temperature, and a storage time of zero means that the microemulsion sample was freshly prepared.

TABLE 3

Adhesion Data for Examples 7-16

| Adhesive Emulsion | Storage Temperature | Storage Time (weeks) | Force (remove from enamel) | Force (remove from dentin) |
|---|---|---|---|---|
| 7 | RT | 0 | 17.8 MPa | 9.3 MPa |
| 7 | RT | 0 | 12.7 MPa | 9.4 MPa |
| 8 | RT | 0 | 17.5 MPa | 7.3 MPa |
| 8 | RT | 0 | 14.0 MPa | 12.1 MPa |
| 9 | RT | 0 | 22.6 MPa | 12.0 MPa |
| 9 | RT | 0 | 18.2 MPa | 13.4 MPa |
| 10 | RT | 0 | 19.3 MPa | 10.5 MPa |
| 10 | RT | 0 | 13.3 MPa | 14.5 MPa |
| 7 | 37° C. | 1 | 17.7 MPa | 10.3 MPa |
| 8 | 37° C. | 1 | 16.0 MPa | 15.0 MPa |
| 9 | 37° C. | 1 | 12.6 MPa | 13.0 MPa |
| 10 | 37° C. | 1 | 18.4 MPa | 16.5 MPa |

TABLE 3-continued

| Adhesion Data for Examples 7-16 | | | | |
|---|---|---|---|---|
| Adhesive Emulsion | Storage Temperature | Storage Time (weeks) | Force (remove from enamel) | Force (remove from dentin) |
| 7 | 45° C. | 0.8 | 9.3 MPa | 8.7 MPa |
| 8 | 45° C. | 0.8 | 13.6 MPa | 11.5 MPa |
| 10 | 45° C. | 0.8 | 13.3 MPa | 14.5 MPa |
| 11 | RT | 0 | 22.3 MPa | 13.3 MPa |
| 12 | RT | 0 | 18.9 MPa | 4.8 MPa |
| 13 | RT | 0 | 16.7 MPa | 9.0 MPa |
| 14 | RT | 0 | 19.2 MPa | 16.2 MPa |
| 15 | RT | 0 | 24.1 MPa | 16.6 MPa |
| 16 | RT | 0 | 27.1 MPa | 21.6 MPa |
| 16 | RT | 3.6 | 22.8 MPa | 13.3 MPa |
| 16 | RT | 4 | 22.9 MPa | 6.5 MPa |
| 14 | 37° C. | 2 | 11.3 MPa | 11.1 MPa |
| 15 | 37° C. | 2 | 17.7 MPa | 8.8 MPa |
| 16 | 37° C. | 2 | 15.3 MPa | 18.2 MPa |
| 16 | 37° C. | 3 | 16.7 MPa | 12.5 MPa |
| 14 | 4° C.-8° C. | 0.9 | 21.0 MPa | 11.3 MPa |
| 15 | 4° C.-8° C. | 0.9 | 25.6 MPa | 12.9 MPa |
| 16 | 4° C.-8° C. | 0.9 | 25.7 MPa | 21.7 MPa |
| 14 | 45° C. | 1 | 11.8 MPa | 9.4 MPa |
| 15 | 45° C. | 1 | 7.4 MPa | 11.5 MPa |
| 16 | 45° C. | 1 | 12.7 MPa | 11.3 MPa |

Examples 17-19

Preparation of Dental Adhesive Microemulsions

Components of the dental adhesive microemulsions of Examples 17-19 include those given in Table 4. The dental adhesive microemulsions of Examples 17-19 were prepared by combining the components, except water, in the amounts given in Table 4, in a vial and using a vortex mixer to prepare a homogeneous mixture. To the composition of Example 19 was then added triphenylantimony (0.01 g). Then CPQ (0.26 g), EDMAB (0.2 g), DPIHFP (0.18 g), and 2-ethyl-9,10-dimethoxyanthracene (0.015 g) were each added to each mixture and the vortex mixer was again used to prepare a homogeneous mixture. Water was then added dropwise with gentle mixing to afford the dental adhesive microemulsions. In Table 4, "n/a" means that the component was not combined in the dental adhesive microemulsion.

TABLE 4

| Compositions of Examples 17-19 | | | |
|---|---|---|---|
| | Example | | |
| Component | 17 | 18 | 19 |
| BisGMA | 2.0 g | 2.5 g | 2.5 g |
| MHP | 1.5 g | 0.5 g | 0.5 g |
| 2-HPM | 1.0 g | 1.0 g | 1.0 g |
| 3KMPS | 0.5 g | n/a | n/a |
| MA | 1.0 g | 0.55 g | 0.55 g |
| HEMA | 1.0 g | 2.5 g | 2.5 g |
| Ethanol | 3.0 g | 4.0 g | 4.0 g |
| Water | 3.0 g | 3.0 g | 3.0 g |
| Example 3 | 2.5 g | n/a | 2.5 g |
| CN2301 | n/a | 3.0 g | n/a |

The dental adhesive microemulsions of Examples 17 and 18 were evaluated using the Adhesion Test described above. The Adhesion Test was conducted using microemulsions stored for a time and at a temperature as indicated in Table 5. The adhesion data are given in Table 5. In Table 5, "RT" means room temperature, and a storage time of zero means that the emulsion sample was freshly prepared.

TABLE 5

| Adhesion Data for Examples 17 and 18. | | | | |
|---|---|---|---|---|
| Adhesive Emulsion | Storage Temperature | Storage Time (weeks) | Force (remove from enamel) | Force (remove from dentin) |
| 17 | RT | 0 | 20.8 MPa | 13.7 MPa |
| 17 | RT | 1 | 20.4 MPa | 17.2 MPa |
| 17 | RT | 2 | 18.9 MPa | 12.9 MPa |
| 17 | RT | 3 | 25.6 MPa | 13.0 MPa |
| 17 | RT | 4 | 21.5 MPa | 8.7 MPa |
| 17 | RT | 5.5 | 24.8 MPa | 14.4 MPa |
| 17 | RT | 7 | 20.9 MPa | 9.3 MPa |
| 17 | RT | 8 | 21.7 MPa | 18.0 MPa |
| 17 | 37° C. | 0.7 | 22.3 MPa | 16.7 MPa |
| 17 | 37° C. | 1.7 | 21.5 MPa | 13.4 MPa |
| 17 | 37° C. | 3 | 19.9 MPa | 17.6 MPa |
| 17 | 37° C. | 4 | 15.9 MPa | 13.6 MPa |
| 17 | 37° C. | 5.5 | 17.7 MPa | 13.1 MPa |
| 17 | 37° C. | 7 | 18.8 MPa | 11.3 MPa |
| 17 | 37° C. | 8 | 12.6 MPa | 12.9 MPa |
| 17 | 37° C. | 10 | 13.0 MPa | 9.7 MPa |
| 17 | 45° C. | 0.7 | 17.8 MPa | 15.1 MPa |
| 17 | 45° C. | 1.7 | 10.6 MPa | 12.9 MPa |
| 17 | 45° C. | 3 | 10.0 MPa | 14.9 MPa |
| 18 | RT | 0 | 23.1 MPa | 20.6 MPa |
| 18 | RT | 2 | 20.0 MPa | 16.7 MPa |
| 18 | RT | 3 | 18.8 MPa | 18.0 MPa |
| 18 | RT | 4 | 20.6 MPa | 16.9 MPa |
| 18 | 37° C. | 3 | 18.6 MPa | 13.5 MPa |
| 18 | 37° C. | 4 | 14.2 MPa | 12.9 MPa |
| 18 | 45° C. | 1 | 18.2 MPa | 16.2 MPa |
| 18 | 45° C. | 2 | 16.1 MPa | 16.7 MPa |
| 18 | 45° C. | 3 | 17.4 MPa | 11.1 MPa |
| 18 | 45° C. | 4 | 15.7 MPa | 14.6 MPa |

Examples 20-30

Preparation of Dental Adhesive Microemulsions

The dental adhesive microemulsion compositions of Examples 20-30 were prepared by combining in each of seven vials MDP (1.5 g), TEGDMA (1.0 g), bisGMA (2.0 g), ethanol (2.5 g), HEMA (1.5 g), and MA (0.5 g). For the composition of Example 20, TMPTMA (1.4 g) and CN2302 (2.5 g) was added to the vial. For the composition of Example 21, TMPTMA (1.4 g) and CN2302 (3.5 g) were added to the vial. For the composition of Example 22, the product of Example 3 (2.5 g) and CN2302 (1.4 g) were added to the vial. For the composition of Example 23, TMPTMA (1.4 g) and CN2301 (2.5 g) were added to the vial. For the composition of Example 24, TMPTMA (1.4 g) and CN2301 (3.5 g) were added to the vial. For the composition of Example 25, TMPTMA (1.4 g) and CN2300 (2.5 g) were added to the vial. For the composition of Example 26, TMPTMA (1.4 g), the product of Example 3 (1.0 g) and CN2301 (2 g) were added to the vial. The contents of each vial were mixed using a vortex mixer. To each vial there were then added CPQ (0.25 g), EDMAB (0.2 g), DPIHFP (0.18 g), and 2-ethyl-9,10-dimethoxyanthracene (0.015 g) and the contents of each vial was again mixed using a vortex mixer. To each vial there was then added, dropwise, water (3.0 g) with gentle mixing to afford the dental adhesive microemulsions.

The dental adhesive microemulsions of Examples 20-30 were evaluated using the Adhesion Test described above. The Adhesion Test was conducted using freshly-prepared microemulsions (i.e., the emulsions had not been stored). The adhesion data are given in Table 6.

TABLE 6

| Adhesion Data for Examples 20-30. | | |
|---|---|---|
| Adhesive Emulsion | Force (remove from enamel) | Force (remove from dentin) |
| 20 | 18.3 MPa | 19.4 MPa |
| 21 | 17.7 MPa | 18.5 MPa |
| 22 | 22.4 MPa | 9.5 MPa |
| 23 | 23.1 MPa | 21.6 MPa |
| 24 | 24.9 MPa | 24.4 MPa |
| 25 | 20.4 MPa | 23.9 MPa |
| 26 | 25.0 MPa | 21.2 MPa |
| 27 | 19.7 MPa | 12.9 MPa |
| 28 | 16.9 MPa | 5.6 MPa |
| 29 | 15.2 MPa | 13.4 MPa |
| 30 | 19.9 MPa | 8.8 MPa |

Additional samples of the adhesive microemulsions of Examples 20 and 21 were stored at 4° C.-8° C. for one week and were then evaluation using the Adhesion Test. For the microemulsion of Example 20, the forces required to pull the pad of cured restorative off of the enamel and the dentin were 15.9 MPa and 21.8 MPa, respectively. For the microemulsion of Example 21, the forces required to pull the pad of cured restorative off of the enamel and the dentin were 19.0 MPa and 16.2 MPa, respectively.

Examples 31-34

Preparation of Dental Adhesive Microemulsions

The dental adhesive microemulsion compositions of Examples 31-34 were prepared by combining in each of four vials TMPTMA (1.4 g), MDP (1.85 g), TEGDMA (1.0 g), BisGMA (2.0 g), ethanol (2.5 g), HEMA (1.5 g), and MA (0.5 g). For the composition of Example 31, CN2301 (2.5 g) was added to the vial. For the composition of Example 32, the product of Example 3 (2.5 g) was added to the vial. For the composition of Example 33, CN2300 (2.5 g) was added to the vial. For the composition of Example 34, the product of Example 3 (1.0 g) and CN2301 (1.5 g) were added to the vial. The contents of each vial were mixed using a vortex mixer. To each vial there were then added CPQ (0.26 g), EDMAB (0.21 g), DPIHFP (0.18 g), and 2-ethyl-9,10-dimethoxyanthracene (0.015 g) and the contents of each vial was again mixed using a vortex mixer. To each vial there was then added, dropwise, water (3.0 g) with gentle mixing to afford the dental adhesive; microemulsions.

The dental adhesive microemulsions of Examples 31-34 were evaluated using the Adhesion Test described above. The Adhesion Test was conducted using freshly-prepared micro-emulsions (i.e., the microemulsions had not been stored). The adhesion data are given in Table 7.

TABLE 7

| Adhesion Data for Examples 31-34 | | |
|---|---|---|
| Adhesive Emulsion | Force (remove from enamel) | Force (remove from dentin) |
| 31 | 8.9 MPa | 3.8 MPa |
| 32 | 15.3 MPa | 3.3 MPa |
| 33 | 12.6 MPa | 5.6 MPa |
| 34 | 13.6 MPa | 5.9 MPa |

Examples 35-38

Preparation of Dental Adhesive Microemulsions

The dental adhesive microemulsion compositions of Examples 35-38 were prepared by combining in each of four vials MDP (1.85 g), BisGMA (2.0 g), ethanol (2.5 g), and MA (0.5 g). For the composition of Example 35, CN2301 (4.5 g) was added to the vial. For the composition of Example 36, the product of Example 3 (4.5 g) was added to the vial. For the composition of Example 37, CN2300 (4.5 g) was added to the vial. For the composition of Example 38, the product of Example 3 (2.0 g) and CN 2301 (2.5 g) were added to the vial. The contents of each vial was mixed using a vortex mixer. To each vial there were then added CPQ (0.23 g), EDMAB (0.18 g), DPIHFP (0.16 g), and 2-ethyl-9,10-dimethoxyanthracene (0.015 g) and the contents of each vial was again mixed using a vortex mixer. To each vial there was then added, dropwise, water (3.0 g) with gentle mixing to afford the dental adhesive microemulsions.

The dental adhesive microemulsions of Examples 35-38 were evaluated using the Adhesion Test described above. The Adhesion Test was conducted using freshly-prepared micro-emulsions (i.e., the microemulsions had not been stored). The adhesion data are given in Table 8.

TABLE 8

| Adhesion Data for Examples 35-38. | | |
|---|---|---|
| Adhesive Emulsion | Force (remove from enamel) | Force (remove from dentin) |
| 35 | 19.0 MPa | 4.0 MPa |
| 36 | 10.9 MPa | 3.0 MPa |
| 37 | 19.6 MPa | 4.9 MPa |
| 38 | 13.5 MPa | 3.4 MPa |

Examples 39-41

Preparation of Dental Adhesive Microemulsions

The dental adhesive microemulsion compositions of Examples 39-41 were prepared by combining in each of three vials TMPTMA (1.4 g), TEGDMA (1.0 g), BisGMA (2.0 g), ethanol (2.5 g), HEMA (1.5 g), and MA (0.5 g). For the composition of Example 39, MDP (1.85 g) and the product of Example 3 (2.5 g) were added to the vial. For the composition of Example 40, MOP (1.85 g) and the product of Example 3 (2.5 g) were added to the vial. For the composition of Example 41, MHP (1.85 g) and the product of Example 3 (3.5 g) were added to the vial. The contents of each vial were mixed using a vortex mixer. To each vial there were then added CPQ (0.25 g), EDMAB (0.20 g), DPIHFP (0.18 g), and 2-ethyl-9,10-dimethoxyanthracene (0.015 g) and the contents of each vial was again mixed using a vortex mixer. To each vial there was then added, dropwise, water (3.0 g) with gentle mixing to afford the dental adhesive microemulsions.

The dental adhesive microemulsions of Examples 39-41 were evaluated using the Adhesion Test described above. The Adhesion Test was conducted using freshly-prepared micro-emulsions (i.e., the emulsions had not been stored). Using the microemulsion of Example 39, the forces required to pull the pad of cured restorative from enamel and from dentin were 14.6 MPa and 2.7 MPa, respectively. Using the microemulsion of Example 40, the forces required to pull the pad of cured restorative from enamel and from dentin were 20.5

MPa and 4.3 MPa, respectively. Using the microemulsion of Example 41, the forces required to pull the pad of cured restorative from enamel and from dentin were 20.2 MPa and 7.5 MPa, respectively. A separate evaluation of the microemulsion of Example 41 was carried out, and the forces required to pull the pad of cured restorative from enamel and from dentin were 19.2 MPa and 1.6 MPa, respectively.

Comparative Examples 1 and 2

Components of the dental adhesive emulsions of Comparative Examples 1 and 2 include those given in Table 9. The dental adhesive emulsions of Comparative Examples 1 and 2 were prepared by combining the components, except the zirconia sol (in the case of Comparative Example 1) or water (in the case of Comparative Example 2), in the amounts given in Table 9, in a vial and using a vortex mixer to prepare a homogeneous mixture. Then CPQ (0.26 g), EDMAB (0.21 g), DPIHFP (0.18 g), and 2-ethyl-9,10-dimethoxyanthracene (0.015 g) were each added to the mixture and the vortex mixer was again used to prepare a homogeneous mixture. The zirconia sol (Comparative Example 1) or water (Comparative Example 2) was then added dropwise with gentle mixing to afford the dental adhesive emulsions. In Table 9, "n/a" means that the component was not combined in the dental adhesive emulsion.

TABLE 9

Compositions of Comparative Examples 1 and 2.

| Component | Comparative Example 1 | Comparative Example 2 |
|---|---|---|
| TMPTMA | 2.0 g | 1.0 g |
| MHP | 0.7 g | 1.0 g |
| TEGDMA | 1.7 g | 1.4 g |
| BisGMA | 1.4 g | 1.4 g |
| Ethanol | 2.0 g | 1.4 g |
| HEMA | 1.0 g | 1.0 g |
| Water | n/a | 1.0 g |
| Zirconia sol | 2.0 g | n/a |
| 1,3-BDDM | n/a | 0.7 g |
| MA | n/a | 0.5 g |
| BH2003 | n/a | 2.5 g |

The dental adhesive emulsions of Comparative Examples 1 and 2 were evaluated using the Adhesion Test described above. The Adhesion Test was conducted using freshly-prepared emulsions (i.e., the emulsions had not been stored). Using the emulsion of Comparative Example 1, the forces required to pull the pad of cured restorative from enamel and from dentin were 14.6 MPa and 9.9 MPa, respectively. Using the emulsion of Comparative Example 2, the forces required to pull the pad of cured restorative from enamel and from dentin were 6.9 MPa and 12.8 MPa, respectively.

Examples 42-44

Preparation of Dental Adhesive Microemulsions Including SR534

Components of the dental adhesive microemulsions of Examples 42-44 include those given in Table 10. The dental adhesive microemulsions of Examples 42-44 were prepared by combining the components, except water, in the amounts given in Table 10, in a vial and using a vortex mixer to prepare a homogeneous mixture. Then CPQ (0.24 g), EDMAB (0.19 g), DPIHFP (0.16 g), triphenylantimony (0.005 g), and EDMA (0.015 g) were each added to the mixture and the vortex mixer was again used to prepare a homogeneous mixture. Water was then added dropwise with gentle mixing to afford the dental adhesive emulsions. In Table 10, "n/a" means that the component was not combined in the dental adhesive microemulsion.

TABLE 10

Compositions of Examples 42-44.

| Component | 42 | 43 | 44 |
|---|---|---|---|
| Example 3 | 0.77 g | 2.1 g | 0.77 g |
| CN2301 | 0.77 g | n/a | 0.77 g |
| SR534 | 2.3 g | 0.85 g | 2.3 g |
| bisGMA | 1.53 g | 1.7 g | 1.53 g |
| MHP | 1.1 g | 0.85 g | 1.1 g |
| HEMA | 2.0 g | 2.1 g | 2.0 g |
| MA | 0.45 g | 0.5 g | 0.45 g |
| 2HPM | 1.15 g | n/a | n/a |
| AA/ITA/IEM | n/a | 0.85 g | 1.15 g |
| DMAPM | 0.1 g | 0.1 g | 0.1 g |
| Ethanol | 3.0 g | 3.4 g | 3.0 g |
| Water | 2.3 g | 2.55 g | 2.3 g |

The dental adhesive microemulsions of Examples 42-44 were evaluated using the Adhesion Test described above. The Adhesion Test was conducted using microemulsions stored for a time and at a temperature as indicated in Table 11. The data are given in Table 11. In Table 11, "RT" means room temperature.

TABLE 11

Adhesion Data for Examples 42-43.

| Adhesive Emulsion | Storage Temperature | Storage Time (week) | Force (remove from enamel) | Force (remove from dentin) |
|---|---|---|---|---|
| 42 | RT | 0.43 | 17.6 MPa | 16.8 MPa |
| 42 | RT | 1 | 13.9 MPa | 25.0 MPa |
| 42 | RT | 2 | 19.4 MPa | 23.1 MPa |
| 42 | RT | 3 | 21.1 MPa | 20.8 MPa |
| 42 | RT | 4 | 16.8 MPa | 20.3 MPa |
| 42 | RT | 5 | 21.5 MPa | 16.6 MPa |
| 42 | RT | 6 | 18.6 MPa | 17.2 MPa |
| 42 | RT | 7 | 20.1 MPa | 21.8 MPa |
| 42 | 37° C. | 0.43 | 15.0 MPa | 14.8 MPa |
| 42 | 37° C. | 2 | 17.3 MPa | 22.1 MPa |
| 42 | 37° C. | 3 | 17.7 MPa | 17.3 MPa |
| 42 | 37° C. | 4 | 13.1 MPa | 19.7 MPa |
| 42 | 37° C. | 5 | 14.5 MPa | 18.4 MPa |
| 42 | 37° C. | 6 | 12.2 MPa | 20.9 MPa |
| 42 | 37° C. | 7 | 18.8 MPa | 19.1 MPa |
| 42 | 45° C. | 0.43 | 17.8 MPa | 17.4 MPa |
| 42 | 45° C. | 2 | 14.0 MPa | 18.8 MPa |
| 42 | 45° C. | 3 | 19.1 MPa | 14.7 MPa |
| 42 | 45° C. | 3.43 | 11.9 MPa | 20.5 MPa |
| 42 | 45° C. | 4 | 15.3 MPa | 19.9 MPa |
| 42 | 45° C. | 5 | 12.0 MPa | 15.8 MPa |
| 42 | 45° C. | 6 | 12.7 MPa | 18.3 MPa |
| 42 | 45° C. | 7 | 12.5 MPa | 9.9 MPa |
| 43 | 37° C. | 1.57 | 15.5 MPa | 9.8 MPa |
| 43 | 45° C. | 1.57 | 15.4 MPa | 10.0 MPa |
| 44 | RT | 3.57 | 17.3 MPa | 19.7 MPa |
| 44 | RT | 6 | 21.1 MPa | 18.6 MPa |
| 44 | RT | 7 | 15.5 MPa | 19.6 MPa |
| 44 | 37° C. | 1.57 | 10.8 MPa | 17.6 MPa |
| 44 | 37° C. | 3.57 | 12.3 MPa | 19.0 MPa |
| 44 | 37° C. | 6 | 20.3 MPa | 18.4 MPa |
| 44 | 37° C. | 7 | 16.6 MPa | 19.1 MPa |
| 44 | 45° C. | 1.57 | 14.1 MPa | 17.2 MPa |
| 44 | 45° C. | 2 | 20.3 MPa | 20.2 MPa |
| 44 | 45° C. | 3.57 | 11.5 MPa | 19.3 MPa |
| 44 | 45° C. | 6 | 10.2 MPa | 16.4 MPa |
| 44 | 45° C. | 7 | 8.9 MPa | 15.2 MPa |

Various embodiments of the invention have been described. These and other embodiments are within the scope of the following claims.

The invention claimed is:

1. An adhesive composition comprising an etchant for a hard tissue surface, at least one multifunctional (meth)acrylate monomer with a functionality greater than 4, wherein the monomer is selected from the group consisting of acrylates and methacrylates derived from a hyperbranched dendritic polyester polyol, and water, wherein the adhesive composition is a water-in-oil emulsion.

2. The composition of claim 1, wherein the acrylates have a functionality of 8 to 16, and wherein the methacrylates have a functionality of 6 to 32.

3. The composition of claim 1, wherein the etchant is selected from the group consisting of 6-methacryloxyhexyl phosphate (MHP) and 10-methacryloxydecyl phosphate (MDP).

4. The composition of claim 1, wherein the composition is a microemulsion.

5. The composition of claim 4, wherein the microemulsion has a water droplet size of less than about 100 nm.

6. The composition of claim 1, further comprising a photopolymerizable compound is selected from the group consisting of trimethylolpropane trimethacrylate (TMPTMA) and triethyleneglycol dimethacrylate (TEGDMA).

7. The composition of claim 1, further comprising a monomer selected from the group consisting of bis-GMA and UDMA.

8. The composition of claim 1, further comprising a penetrant for a hard tissue surface, wherein the penetrant comprises hydroxyethyl methacrylate (HEMA).

9. A dental adhesive composition, comprising:

(a) 5-25 wt % of a multifunctional (meth)acrylate monomer with a functionality greater than 4, wherein the monomer is derived from a hyperbranched dendritic polyester polyol;

(b) 10-25 wt % water;

(c) 0-25 wt % of a co-solvent selected from the group consisting of ethyl alcohol, ethyl acetate, and isopropanol; and (d) 5-11 wt % of an etchant for at least one of dentin and enamel, wherein the dental adhesive composition is a microemulsion.

10. A method comprising applying the adhesive composition of claim 9 to a dental structure surface.

* * * * *

UNITED STATES PATENT AND TRADEMARK OFFICE

CERTIFICATE OF CORRECTION

PATENT NO. : 8,076,389 B2
APPLICATION NO. : 12/520703
DATED : December 13, 2011
INVENTOR(S) : Prabhakara S Rao It is certified that error appears in the above-identified patent and that said Letters Patent is hereby corrected as shown below:

Column 8
Line 44 Delete “pheny-1” and insert -- phenyl --, therefor.

Column 10
Line 48 Delete “hydroxylpropyl)” and insert -- hydroxypropyl) --, therefor.

Column 11
Line 9 Delete “Mania;” and insert -- titania; --, therefor.

Signed and Sealed this
Twenty-fourth Day of January, 2012

David J. Kappos
*Director of the United States Patent and Trademark Office*